United States Patent
Liu et al.

(10) Patent No.: US 11,232,370 B2
(45) Date of Patent: Jan. 25, 2022

(54) BIOMETRIC DATA TO FACILITATE LEARNING

(71) Applicant: Hewlett-Packard Development Company, L.P., Fort Collins, CO (US)

(72) Inventors: Lei Liu, Palo Alto, CA (US); Tong Zhang, Palo Alto, CA (US); Steven J Simske, Ft. Collins, CO (US)

(73) Assignee: Hewlett-Packard Development Company, L.P., Spring, TX (US)

(*) Notice: Subject to any disclaimer, the term of this patent is extended or adjusted under 35 U.S.C. 154(b) by 969 days.

(21) Appl. No.: 15/746,312

(22) PCT Filed: Aug. 14, 2015

(86) PCT No.: PCT/US2015/045348
§ 371 (c)(1),
(2) Date: Jan. 19, 2018

(87) PCT Pub. No.: WO2017/030539
PCT Pub. Date: Feb. 23, 2017

(65) Prior Publication Data
US 2018/0218288 A1    Aug. 2, 2018

(51) Int. Cl.
*G06N 20/00*    (2019.01)
*G16H 50/20*    (2018.01)
*G16Z 99/00*    (2019.01)
*G16H 10/60*    (2018.01)

(52) U.S. Cl.
CPC ............ *G06N 20/00* (2019.01); *G16H 10/60* (2018.01); *G16H 50/20* (2018.01); *G16Z 99/00* (2019.02)

(58) Field of Classification Search
CPC ............................. G06N 20/00; G16H 10/60
See application file for complete search history.

(56) References Cited

U.S. PATENT DOCUMENTS

| | | | |
|---|---|---|---|
| 2003/0135097 A1 | 7/2003 | Wiederhold et al. | |
| 2006/0084847 A1 | 4/2006 | Reed et al. | |
| 2008/0228868 A1 | 9/2008 | Sivakoff | |
| 2014/0107494 A1 | 4/2014 | Kato et al. | |
| 2014/0119563 A1 | 5/2014 | Caskey et al. | |
| 2014/0188770 A1 | 7/2014 | Agrafioti et al. | |
| 2015/0223731 A1* | 8/2015 | Sahin | A61B 5/1123 600/301 |
| 2018/0218288 A1* | 8/2018 | Liu | G06N 20/00 |

FOREIGN PATENT DOCUMENTS

| | | |
|---|---|---|
| EP | 399513 A1 | 12/2011 |
| EP | 2399513 A1 | 12/2011 |
| KR | 20140002369 | 6/2012 |
| KR | 10-2014-0114588 A | 9/2014 |

OTHER PUBLICATIONS

Kanneh, A et al, "Haptics and the Biometric Authentication Challenge", Mar. 16, 2014.

* cited by examiner

*Primary Examiner* — David E Choi
(74) *Attorney, Agent, or Firm* — HP Inc. Patent Department

(57) ABSTRACT

A system that uses biometric data to facilitate learning is provided herein. The system receives at least two data points via a biometric sensor. Information is extracted from the at least two data points and a set of features are identified. Data analysis is then performed on the set of features.

16 Claims, 5 Drawing Sheets

BIOMETRIC DATA TO FACILITATE LEARNING

BACKGROUND

Biometry is the technology of statistically analyzing biological data. Any data created during a biometric process is named as biometric data, which usually refers to the unique physical and/or logical characteristics or traits of each person's human body. Examples of biometric test devices to obtain biometric data include electroencephalogram (EEG) sensors, Electrocardiogram (ECG) sensors, heart rate monitors, and thermometers.

BRIEF DESCRIPTION OF THE DRAWINGS

The following detailed description references the drawings, wherein.

DETAILED DESCRIPTION

Figure 1:
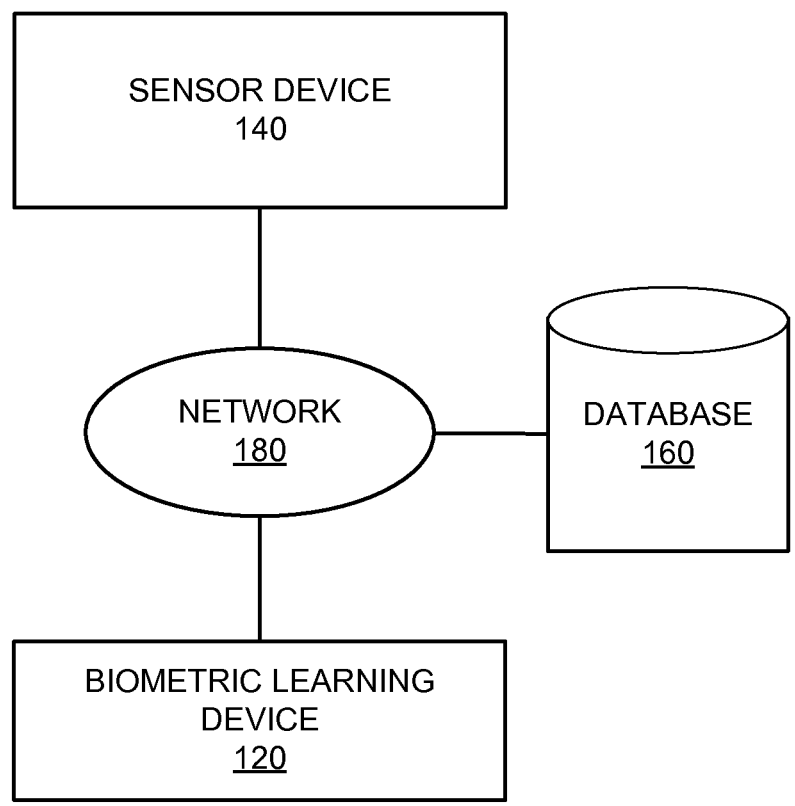
FIG. 1 illustrates a block diagram of a system that uses biometric data to facilitate learning according to an example.

The following detailed description refers to the accompanying drawings. Wherever possible, the same reference numbers are used in the drawings and the following description to refer to the same or similar parts. While several examples are described in this document, modifications, adaptations, and other implementations are possible. Accordingly, the following detailed description does not limit the disclosed examples. Instead, the proper scope of the disclosed examples may be defined by the appended claims.

Biometric data analytics have been mostly used in computer science as a form of identification and access control for security and accessing privileges on devices or at locations. Mining biometric data for identification and access control purposes has improved in accuracy in the past few years. Use of biometric data has also expanded and it is now frequently used to identify individuals in groups that are under surveillance using for example, fingerprint and facial recognition technology. Other forms of biometric data that may be collected include heart rate, temperature, galvanic skin responses, neurological responses, and facial changes.

Existing educational data analysis techniques have focused on analyzing learners' historical logs or reading behaviors to facilitate the education process. Biometric data, which is directly generated from each individual learner, has the ability to help us provide a better education experience. Examples relate to use of biometric data to facilitate learning. At least two data points are received via a biometric sensor. Data is extracted from the at least two data points and a set of features are identified. Data analysis is then performed on the set of features. Examples provided herein use biometric data analysis to facilitate the learning and/or training process by mining the relationships between biometric data and human content consumption behavior during learning process to facilitate the human learning process.

As used herein, "learning data" refers to data associated with content consumption, such as learning, education, reading, and/or training. For example, learning data may include data specifically related to biometric measurements such as heart rate, temperature, galvanic skin responses, neurological responses, and/or facial changes. Learning data does not include additional data or information, such as noise and/or artifact data, that may be transmitted from sensors with the biometric measurements.

As used herein, "unnecessary sensor data" refers to noise, artifact, or non-biometric data collected. For example, the unnecessary sensor data may be removed without compromising the quality of the biometric data collected and used in the analysis.

Referring now to the drawings, FIG. 1 illustrates a block diagram of a system for using biometric data to facilitate learning according to an example. System 100 may be implemented in a number of different configurations without departing from the scope of the disclosed examples. In FIG. 1, system 100 may include a biometric learning device 120, a sensor device 140, a database 160, and a network 180 for connecting biometric learning device 120 with database 160 and/or sensor device 140.

Biometric learning device 120 may be a computing system that performs various functions consistent with disclosed examples, such as using biometric data to facilitate learning. For example, biometric learning device 120 may be a desktop computer, a laptop computer, a tablet computing device, a mobile device, a server, and/or any other type of computing device. In some examples, biometric learning device 120 may obtain at least two data points via a biometric sensor or a plurality of biometric sensors. Examples of the data points may include heart rate, temperature, galvanic skin responses, neurological responses, and/or facial changes. Biometric learning device 120 may receive the data points from at least one sensor device 140. For example, at least one of the two data points obtained may be from a facial sensor or a wearable device. The other of the two data points may be from facial sensors, wearable devices, or other sensors such as mobile sensors, heart rate monitors, thermometers, and sensors for capturing EEG and ECG signals.

Biometric learning device 120 may also extract a collection of learning data from the at least two data points. For example, biometric learning device 120 may remove unnecessary sensor data such as noise, artifact, or non-biometric data collected from the sensor device 140.

Using the collection of learning data, biometric learning device 120 may identify a set of features and perform feature reduction on the set of features. For example, the feature reduction may generate a feature matrix and perform feature reduction on the feature matrix. Moreover, the set of features may be mapped to the at least two learning characteristics and a classifier may be trained to distinguish between the at least two learning characteristics.

Biometric learning device 120 may analyze the set of features selected. For example, biometric learning device 120 may apply a machine learning modeling executed by a processor to the feature matrix and output discovered correlations, associations, and/or patterns. In a further example, biometric learning device 120 may apply a predictive model to the feature matrix to identify relationships between the set of features and a learning characteristic. A subset of the set of features may then be correlated with at least two learning characteristics using predictive modeling or feature reduction using the subset of the set of features and the collection of learning data without applying additional functions. Examples of biometric learning device 120 and certain functions that may be performed by biometric learning device 120 are described in greater detail below with respect to, for example, FIGS. 2-5.

Sensor device 140 may be any device that maintains, receives, or transfers data from a data collection. Sensor device 140 may be a scanning, monitoring, or sensing device with sensors that are transduced to a digital signal, such as piezoelectric or chemoelectric signals. For example, the sensor device 140 may be an EEG sensor, ECG sensor, a heart rate monitor, a thermometer, or a computing device, such as a desktop computer, a laptop computer, a tablet computing device, a mobile device, a server, or any other type of computing device connected to a sensor that collects biometric data. Sensor device 140 may receive, transfer, or otherwise access data collections, such as data points used by the biometric learning device 120. For example, sensor device 140 may provide access to data points and other biometric related data that is obtained from a human being. Sensor device 140 may also collect, maintain, query, and/or analyze digital versions of data points collected. Sensor device 140 may include a processor, and may access, via the processor, a digital version of the data collected. Examples of data points are discussed in greater detail below with respect to, for example, FIGS. 2-5.

Database 160 may be any type of storage system configuration that facilitates the storage of data. For example, database 160 may facilitate the locating, accessing, and retrieving of data (e.g., SaaS, SQL, Access, etc. databases, XML files, etc.). Database 160 can be populated by a number of methods. For example, biometric learning device 120 may populate database 160 with database entries generated by biometric learning device 120, and store the database entries in database 160. As another example, biometric learning device 120 may populate database 160 by receiving a set of database entries from another component, a wireless network operator, and/or a user of sensor device 140, and storing the database entries in database 160. In a further example, sensor device 140 may populate database 160. The entries in the database 160 may provide a central repository for data resulting from data processing, such as results of screening data, removing noise and/or artifact data, extracting portions of the biometric data, and modeling results.

The data may be obtained using electronic means, such as through use of an electronic and/or scanning device connected to the biometric learning device and/or sensor device 140. The database entries can contain a plurality of fields, which may include information related to data points, a collection of learning data, features, and learning characteristics. While in the example shown in FIG. 1 database 160 is a single component external to components 120 and 140, database 160 may comprise separate databases and/or may be part of devices 120, 140, and/or another device. In some implementations, database 160 may be managed by components of devices 120 and/or 140 that are capable of accessing, creating, controlling and/or otherwise managing data remotely through network 180.

Network 180 may be any type of network that facilitates communication between remote components, such as biometric learning device 120 and sensor device 140. For example, network 180 may be a local area network (LAN), a wide area network (WAN), a virtual private network, a dedicated intranet, the Internet, and/or a wireless network.

The arrangement illustrated in FIG. 1 is simply an example, and system 100 may be implemented in a number of different configurations. For example, while FIG. 1, shows one biometric learning device 120, sensor device 140, database 160, and network 180, system 100 may include any number of components 120, 140, 160, and 180, as well as other components not depicted in FIG. 1. System 100 may also omit any of components 120, 140, 160, and 180. For example, biometric learning device 120 and sensor device 140 may be directly connected instead of being connected via network 180. As another example, biometric learning device 120 and sensor device 140 may be combined to be a single device.

Figure 2:
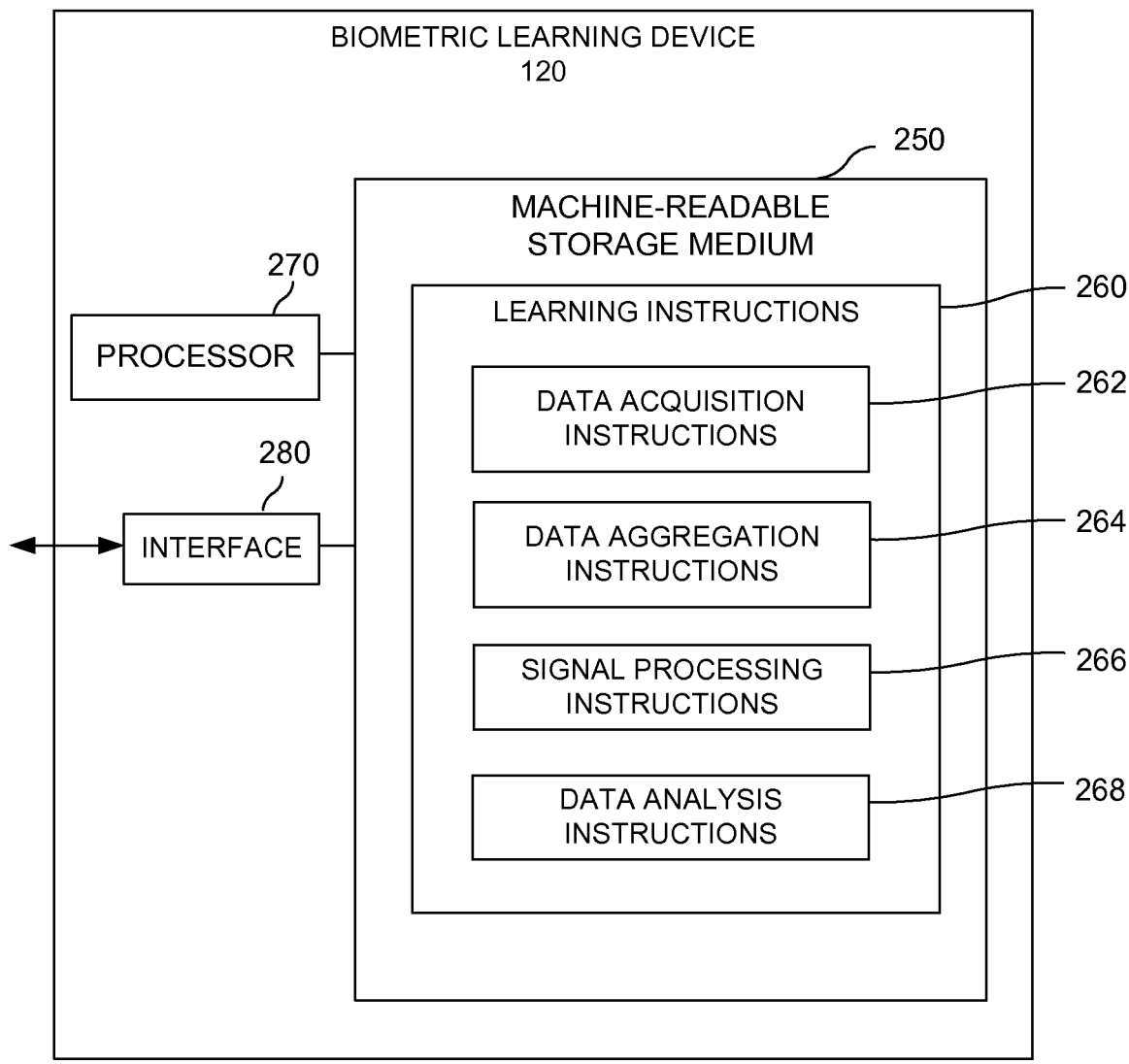
FIGS. 2-3 illustrate block diagrams of biometric learning devices according to examples.
Figure 3:
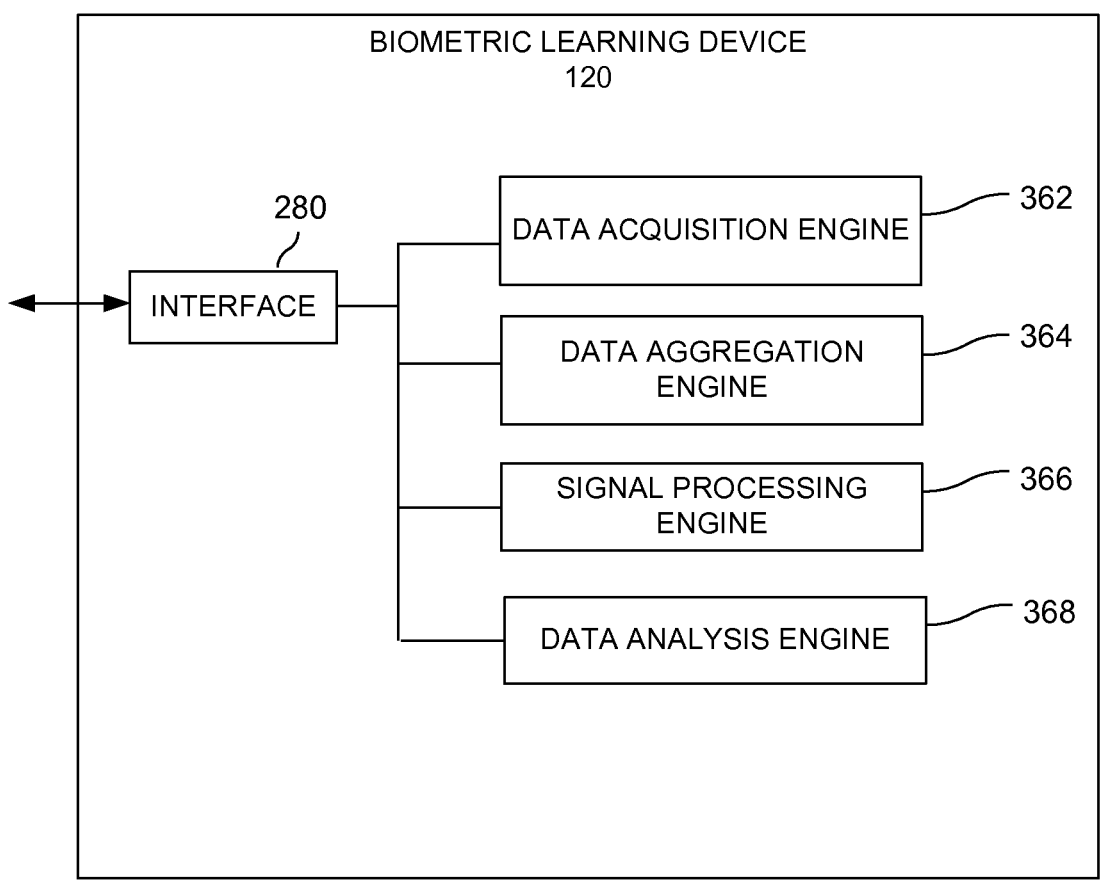

FIGS. 2-3 illustrate block diagrams of biometric learning devices according to examples. Referring to FIG. 2, a biometric learning device 120 is illustrated. In certain aspects, biometric learning device 120 may correspond to multiple biometric learning devices 120 of FIG. 1. Biometric learning device 120 may be implemented in various ways. For example, biometric learning device 120 may be a special purpose computer, a server, a mainframe computer, a computing device executing instructions that receive and process information and provide responses, and/or any other type of computing device. In the example shown in FIG. 2, biometric learning device 120 may include a machine-readable storage medium 250, a processor 270, and an interface 280.

Processor 270 may be at least one processing unit (CPU), microprocessor, and/or another hardware device to execute instructions to perform operations. For example, processor 270 may fetch, decode, and execute learning instructions 260 (e.g., instructions 262, 264, 266, and/or 268) stored in machine-readable storage medium 250 to perform operations related to examples provided herein.

Interface 280 may be any device that facilitates the transfer of information between biometric learning device 120 and other components, such as sensor device 140 and/or database 160. In some examples, interface 280 may include a network interface device that allows devices, such as biometric learning device 120, sensor device 140, and database 160 to receive and send data to and from network 180. For example, interface 280 may retrieve and process data related to using biometric data to facilitate learning from database 160 via network 180.

Machine-readable storage medium 250 may be any electronic, magnetic, optical, or other physical storage device that stores executable instructions. Thus, machine-readable storage medium 250 may be, for example, memory, a storage drive, an optical disc, and/or the like. In some implementations, machine-readable storage medium 250 may be non-transitory, such as a non-transitory computer-readable storage medium, where the term "non-transitory" does not encompass transitory propagating signals. Machine-readable storage medium 250 may be encoded with instructions that, when executed by processor 270, perform operations consistent with the examples herein. For example, machine-readable storage medium 250 may include instructions that perform operations that use biometric data to facilitate learning by receiving at least two data points, extracting a collection of learning data from the at least two data points, identifying a set of features from the collection of learning data and performing feature reduction on the set of features, and analyzing the set of features after the feature reduction to correlate a subset of the set of features to at least two learning characteristics. In the example shown in FIG. 2, machine-readable storage medium 250 may include data acquisition instructions 262, data aggregation instructions 264, signal processing instructions 266, and data analysis instructions 268.

Data acquisition instructions 262 may function to obtain at least two data points from biometric sources. For example, when data acquisition instructions 262 are executed by processor 270, data acquisition instructions 262 may cause processor 270 of biometric learning device 120, and/or another processor to obtain at least two data points from biometric sources, such as biometric sensors. The execution of the data acquisition instructions 262 may also cause processor 270 of biometric learning device 120, and/or another processor to obtain at least one of the at least two data points from a sensor that does not detect EEG signals. Other sensors may include a facial sensor, a heart rate monitor, a thermometer, a mobile sensor, or a wearable device. Examples of the steps involved in obtaining data points are described in further detail below with respect to, for example, FIGS. 4-5.

Data aggregation instructions 264 may function to gather a filtered biometric data set by extracting information from the at least two data points. For example, when data aggregation instructions 264 are executed by processor 270, data aggregation instructions 264 may cause processor 270 of biometric learning device 120, and/or another processor to remove unnecessary sensor data from the at least two data points. Examples of the steps involved in filtering the data points are described in further detail below with respect to, for example, FIGS. 4-5.

Signal processing instructions 266 may function to identify a set of features from the filtered biometric data. For example, when signal processing instructions 266 are executed by processor 270, signal processing instructions 266 may cause processor 270 of biometric learning device 120, and/or another processor to use the set of features to generate a feature matrix and perform feature reduction on the feature matrix. In a further example, the filtered biometric data may be stored as a collection of learning data. The set of features identified from the collection of learning data may be used for feature reduction. Examples of the steps involved in identifying the set of features are described in further detail below with respect to, for example, FIGS. 4-5.

Data analysis instructions 268 may function to analyze the set of features selected. For example, when signal processing instructions 266 are executed by processor 270, signal processing instructions 266 may cause processor 270 of biometric learning device 120, and/or another processor to analyze the set of features after the feature reduction and to correlate the set of features to at least two learning characteristics. For example, the feature reduction may map the set of features to the at least two learning characteristics. The analysis may include applying a predictive model to the feature matrix to identify relationships between the set of features and a learning characteristic. A classifier may then be trained to distinguish between the at least two learning characteristics. The analysis may further include applying a machine learning modeling executed by a processor to a feature matrix and outputting discovered associations or patterns that may be determined without applying additional functions. Examples of the steps involved in analyzing the set of features are described in further detail below with respect to, for example, FIGS. 4-5.

Referring to FIG. 3, biometric learning device 120 is illustrated to include a data acquisition engine 362, a data aggregation engine 364, a signal processing engine 366, and a data analysis engine 368. In certain aspects, biometric learning device 120 may correspond to biometric learning device 120 of FIGS. 1-2. Biometric learning device 120 may be implemented in various ways. For example, biometric learning device 120 may be a computing system and/or any other suitable component or collection of components that facilitate education.

Interface 280 may be any device that facilitates the transfer of information between biometric learning device 120 and external components. In some examples, interface 280 may include a network interface device that allows biometric learning device 120 to receive and send data to and from a network. For example, interface 280 may retrieve and process data related to facilitating education using data from biometric learning device 120, sensor device 140, and/or database 160.

Engines 362, 364, 366, and 368 may be electronic circuitry for implementing functionality consistent with disclosed examples. For example, engines 362, 364, 366, and 368 may represent combinations of hardware devices and instructions to implement functionality consistent with disclosed implementations. For example, the instructions for the engines may be processor-executable instructions stored on a non-transitory machine-readable storage medium and the hardware for the engines may include a processor to execute those instructions. In some examples, the functionality of engines 362, 364, 366, and 368 may correspond to operations performed by biometric learning device 120 of FIGS. 1-2, such as operations performed when learning instructions 260 are executed by processor 270.

In FIG. 3, data acquisition engine 362 may represent a combination of hardware and instructions that performs operations similar to those performed when processor 270 executes data acquisition instructions 262. Similarly, data aggregation engine 364 may represent a combination of hardware and instructions that performs operations similar to those performed when processor 270 executes data aggregation instructions 264, and signal processing engine 366 may represent a combination of hardware and instructions that performs operations similar to those performed when processor 270 executes signal processing instructions 266. Moreover, data analysis engine 368 may represent a combination of hardware and instructions that performs operations similar to those performed when processor 270 executes data analysis instructions 268

Figure 4:
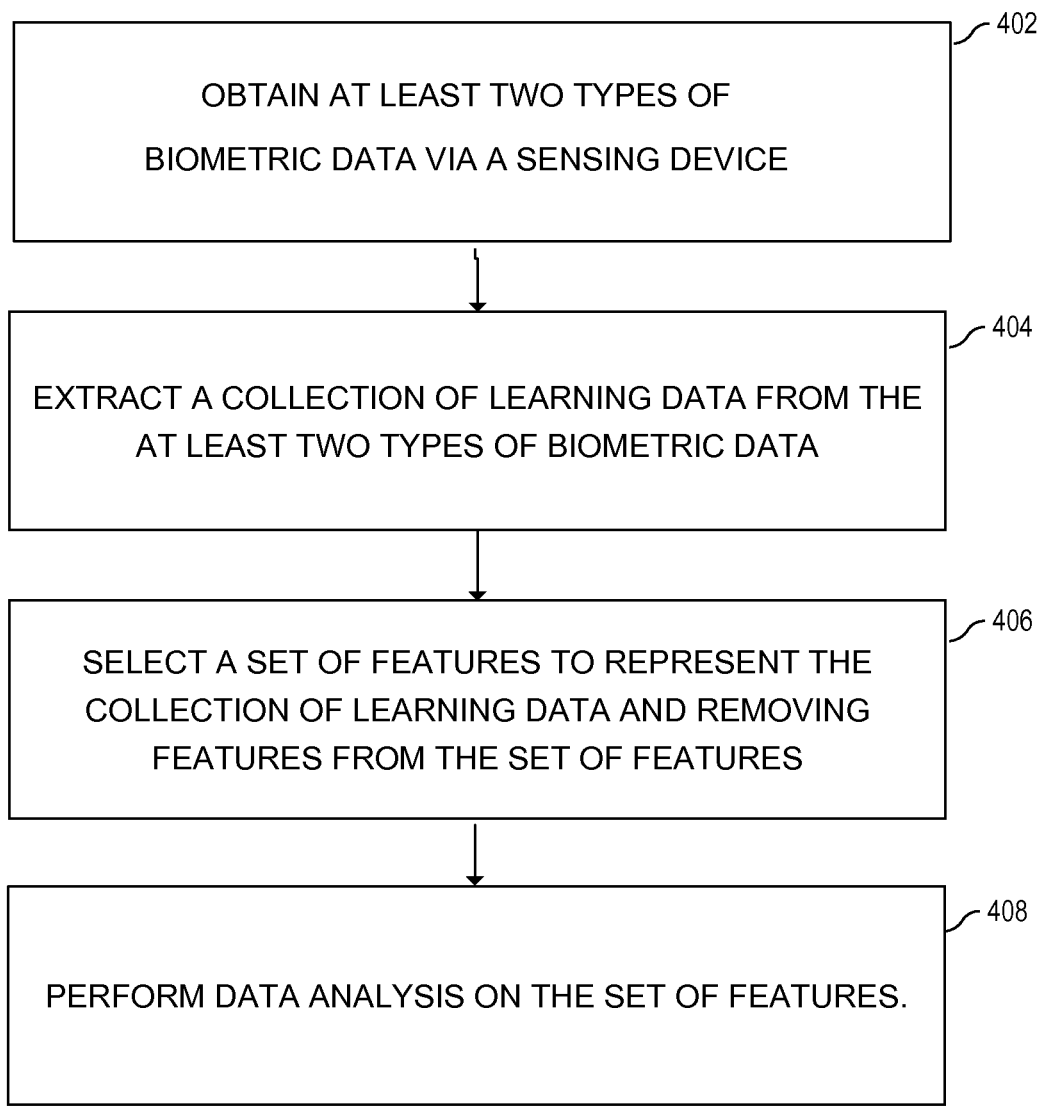
FIG. 4 illustrates a flow chart of a process to use biometric data to facilitate learning according to an example.

FIG. 4 illustrates a flow chart of a process to facilitate education using biometric data according to examples. Although execution of process 400 is described below with reference to system 100, other suitable systems and/or devices for execution of at least one step of process 400 may be used. For example, processes described below as being performed by system 100 may be performed by biometric learning device 120, sensor device 140, and/or any other suitable device or system. Process 400 may be implemented in the form of executable instructions stored on a storage device, such as a machine-readable storage medium, and/or in the form of electronic circuitry.

Referring to FIG. 4, a method to use biometric data to facilitate learning is provided. Process 400 may start by obtaining at least two types of biometric data via a sensing device (step 402). The data may be obtained from a variety of sensors such as mobile sensors, smart watch sensors, facial sensors, heart rate monitors, thermometers, and sensors for capturing EEG and ECG signals. The data may be transferred from sensors to a biometric learning device via wired and/or wireless methods. For example, biometric learning device 120 and/or sensor device 140 of system 100 may query or otherwise access database 160 to obtain biometric data stored in a storage device, such as database 160. The biometric data set may be stored in a storage device, such as database 160, and biometric learning device 120 and/or sensor device 140 may query database 160 to obtain the stored data. In a further example, biometric data may be stored on sensor device 140 and directly associated with sensor device 140, i.e., when self-contained remote sensors are used.

Process 400 may also include extracting a collection of learning data from the at least two types of biometric data (step 404). For example, biometric learning device 120 and/or sensor device 140 may extract a collection of learning data by removing non-related biometric data to create a filtered biometric data set. The filtered biometric data set may be manipulated by extracting the subset of the set of features identified as corresponding to learning characteristics. The filtered biometric data set, the set of features, and the learning characteristics may be stored in a storage device, such as database 160, and biometric learning device 120 and/or sensor devices 140 may query database 160 to obtain the stored data.

Process 400 may also include selecting a set of features to represent the collection of learning data and removing features from the set of features to form a subset of the set of features (step 406). For example, biometric learning device 120 and/or sensor device 140 may remove unnecessary sensor data, such as noise, artifact, and/or non-biometric data collected. The set of features may be stored in a storage device, such as database 160, and biometric learning device 120 and/or sensor device 140 may query database 160 to obtain the set of features.

Process 400 may also include performing data analysis on the subset of the set of features (step 408). For example, biometric learning device 120 and/or sensor device 140 may apply data fusion technology on the subset of the set of features to categorize the collection of learning data for each learner. The categorization of the collection of learning data may include categories corresponding to learning characteristics. Biometric learning device 120 and sensor device 140 may further perform data analysis such as identifying hidden patterns in the subset of the set of features to obtain a learning characteristic or performing predictive modeling on the subset of the set of features to obtain a learning characteristic. Learning characteristics may be stored in a storage device, such as database 160, and biometric learning device 120 and/or sensor device 140 may query database 160 to obtain learning characteristics.

Figure 5:
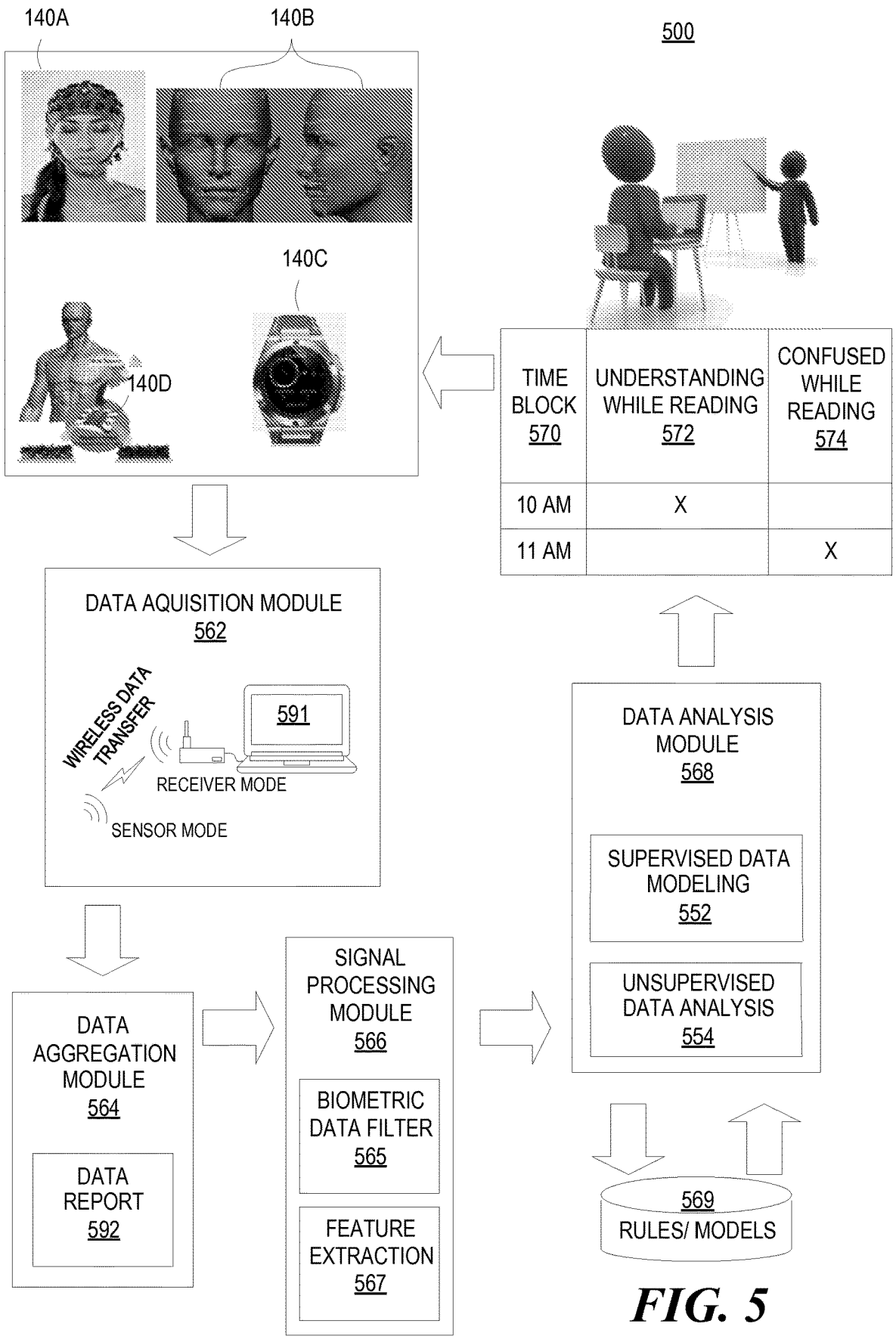
FIG. 5 illustrates a schematic diagram of an overall system architecture for using biometric data to facilitate learning according to an example.

FIG. 5 illustrates a schematic diagram 500 of an overall system architecture for using biometric data to facilitate learning according to an example. Educational data analytics have been primarily focused on learners' body indirect data, including reading logs, reading notes, and/or patterns. Biometric data that is generated directly from each individual person has been ignored. System 500 of FIG. 5 discovers the hidden relations between different brain functions and learning behaviors. Such brain functions are represented by biometric data that are captured from different sensors, including mobile sensors, smart watch sensors, and/or sensors for capturing EEG signals.

System 500 allows each learner to know himself/herself better, encourages each learner to study in the most efficient way, and achieves optimal learning outcomes easier and more efficiently. For example, some people may find that video is easier for them to understand, while others may prefer text. However, no matter which type they prefer, we expect there is a biometric signal difference between "content understood" and "content confusing". Therefore, detecting biometric signal pattern differences can help better understand each learner. A better understanding of each learner allows content to be delivered in a more appropriate way.

The biometric data may be processed using data analytic models and/or machine learning approaches to discover the relationships between biometric signals and learning quality. For example, learners may find they cannot focus, which results in low learning outcomes. Modeling the underlying relations discovered between biometric signals and learning quality may be used during future learning processes to, for example, remind learners to focus or suggest them to have rest if the monitored biometric signals indicate confusion or lack of focus. The relationship between biometric data and human content consumption behaviors in education may also be applied to monitoring the reading progress and/or assessing reading comprehension. The biometric data and its relationship to education may be used to help find the most efficient learning experience, train students how to focus while reading, train students how to extend their attention span, discover personal interest, and/or derive a personalized learning pattern.

The input is students' sensor data acquired during a learning and/or training process. Data acquisition module 562 is responsible for obtaining multiple sources of biometric data via various sensors, such as an EEG sensor 140A, a facial sensor 140B, wearable sensor 140C, and mobile sensor 140D. Data aggregation module 564 compiles biometric data obtained by data acquisition module 562 into an aggregate report 592. Signal processing module 566 has two components, namely, biometric data filtering 565 and feature extraction 567. The purpose of biometric data filtering 565 is to extract relevant information from the data, such as, detecting waves or events captured by the EEG sensors 140A that indicate certain activities of the brain, through signal processing techniques. The purpose of feature extraction 567 is to select the most representative features and perform feature reduction. For example, feature reduction may be performed through statistical analysis, principal component analysis or data summarization. Data analysis module 568 is used to discover hidden patterns or build a predictive model using the biometric data. The details of each component are further discussed below. Modules 562, 564, 566, and 568 may include hardware and instructions of FIGS. 2-3.

Referring to data acquisition module 562, biometric sensors are used to acquire data from a human body. Relevant biometric sensors to this framework include EEG electrodes 140A placed at different locations of the scalp, facial sensors 1408 for capturing facial changes, sensors in wearable devices 140C (e.g. smart watch/wrist band) for temperature, heart rate and/or galvanic skin response.

Data aggregation module 564 receives the biometric data that is captured from the biometric sensors, i.e. 140A-D. Data aggregation module 564 receives the biometric data in a wired or wireless manner, such as from a sensor on a human that is connected to a computing device 591. The biometric data generated from different sensors may be compiled into an aggregated report 592. The aggregate report 592 may be stored in a database 160, such as a local database or on the cloud, as described with respect to FIG. 1. The aggregate report 592 may facilitate data pre-processing and data modeling works. For example, data aggregation module 564 may perform data screening functions, such as to remove noisy data or extract relevant data, to reduce the bandwidth for data transmission and workload for further processing.

Signal processing module 566 may include two components, biometric data filtering 565 and feature extraction 567. During biometric data filtering 565, artifact data is removed from the sensor data. This process enhances the input by filtering out non-related biometric data. For example, the filtering may include removing background noise and/or artifact data. Various filtering techniques may be used, such as, adaptive filtering techniques and filter banks can be applied to detect certain slow waves, fast waves and spikes from biometric signals, such as the EEG signal that may indicate certain brain activities or responses. The process may then discard the signals that are irrelevant.

During feature extraction 567, the biometric data that are remain after filtering non-related biometric data and removing signal noise, may be manipulated by extracting the most representative features, such as, EEG waves, temporal curve of temperature and heart rate, and statistics of such data. The features extracted may not be a subset of the original feature space, but could also be a linear or non-linear combination of multiple features using a kernel track. In addition to selecting the most representative features, another benefit of feature extraction 567 is in reducing feature dimension. Reducing feature dimension may enhance the efficiency of data modeling, and reduce the complexity of predictive model in data modeling processing. Standard feature extraction 567 and reduction analysis include, for example, Principal Component Analysis (PCA), Singular Value Decomposition (SVD), and Latent Semantic Analysis (LSA). Data analysis module 568 may use the processed biometric data from the above modules to facilitate training and education by applying an analysis method to discover patterns between the biometric data and learning characteristics.

For example, signal processing module 566 and data analysis module 568 may apply data fusion technology to better understand each learner using biometric data from multiple devices and/or sensors. Data fusion technology may filter out the unnecessary sensor data, such as noise and artifact data, and combine all biometric features into a single matrix and perform feature analysis on the collective set of all features. Feature analysis may include, for example, feature reduction, feature deduction, correlation, and feature kernel mapping. Then data fusion technology may be used to model the reduced feature matrix with machine learning modeling methods executed by a processor, and output the discovered patterns or rules or apply the learnt predictive models to make the education related intelligent prediction.

Four examples are included below for illustrative purposes. Examples describe the use of deeper biometric data analytics to provide solutions to advanced and personalized questions in an effort to further help a human learning processes.

First Analysis Example

In a first example, a common learning pattern is discovered between every learner's biometric data and learning behaviors, without considering their individual learning difference. System 500 is built to learn which features of EEG signals, facial positions, temperature, heart rate, and/or other biometric data collected by data acquisition module 562 indicate a level of attention during learning, and which features have the ability to differentiate learning states, such as, "reading while understanding content" 572 from "reading while confused with content" 574. In applying an analysis method, any supervised data modeling method 552, such as, Support Vector Machine (SVM), Decision Tree, Random Forest, Bayesian Classifier, Neural Network, or K-Nearest Neighbor (KNN) may be used for this general data modeling mode. The models and rules 569 used for analysis may be stored in a separate database or integrated into data analysis module 568. The predictive model is trained using data from all the learners.

In the example, the supervised model 552 is built by collecting labeled data for the training purpose. Such data is labeled in a task dependent way. For example, to perform a reading assessment by predicting if a learner understands what she is currently reading, biometric data is first segmented into different time blocks 570. Each time block 570, such as time blocks "10 AM" and "11 AM," is associated with one of predefined labels: "understanding while reading" 572 or "confused while reading" 574. The learning state prediction problem is labeled as a binary classification task and the biometric data may be used to classify the learner as understanding 572 or being confused 574 during each time block 570. Time block 570 intervals and tasks, "understanding while reading" 572 or "confused while reading" 574 are examples of the intervals that may be used and the types of learning characteristics or tasks that may be assigned during a learning or training session. Other information, such as the learner's identification and settings for the learner's biometric sensors may also be collected and/or displayed to facilitate learning.

The classification task may be solved with the following steps that use SVM as an example. First signal processing is performed to remove the noise and not useful signal information, for example with data aggregate module 564. Next, any feature selection or extraction technique is applied to reduce feature dimension, using, for example, signal processing module 566. Examples of extraction techniques may include SVD or Tf*Idf. Using SVD as an example, the extraction technique is defined as: $X=U\Sigma W^T$, where the original data matrix $X \in Rn \times d$ is mapped from an original space of d variables to a new space of p variables in $\hat{X}=U\Sigma \in R^{n \times p}$, where p<d. Then, using the new transformed data matrix X', a binary classifier is trained to distinguish the learning state "confused while reading" 574 and "understanding while reading" 572 as determined in data analysis module 568. Since the biometric data may not be linearly separable after processing, a kernel track may be applied to map the biometric data to a dimension where the data could be linearly separable.

For example, kernel track may be applied with the widely used RBF kernel defined as: $(x,x')=\exp(-\|x-x'\|^2/2\sigma^2)$. Instead of using any existing kernel methods, an optimization objective function and learn a kernel method that work best on any given data set may be applied. For example, learning SVM classifier f: $R^p \rightarrow \{1,2\}$ that accurately maps the feature vector of a learner's biometric data to its class label 1 or 2, where we use 1 for "understanding while reading", 2 for "confused while reading". Trained classifier (.) is applied to predict if a learner is confused or understanding in future reading process. Although predicting the learning states "understanding while reading" or "confused while reading" is a binary classification task, the steps could easily extend to multi-class classification or regression tasks. For example, if we want to know the specific levels of comprehension, then a regression task may be used. In the example of regression, the output may be values between 0 and 1 to indicate levels of comprehension, where 1 means completely understand, 0 means completely confused, and values between 0 and 1 indicate partial levels of understanding and confusion.

Second Analysis Example

In a second example, each learner's individual characteristics could be modeled to make a model discovery for each specific learner. Customizing the model for every learner is useful since every one learns differently. For example, the analysis could monitor the personalized reading progress, in order to find the most efficient learning experience for each individual learner. The analysis could also be used to train each student how to focus based on her historical labeled reading behavior, perform a personalized reading assessment, train students how to extend their attention span, discover personal interests, derive personalized learning patterns, determine the uniqueness of learning patterns for each individual, and determine the value of personalized learning patterns compared to a generic, non-personalized approach.

The analysis may include any supervised data modeling 552 that considers user profile and is predictive. For the personalized data modeling mode, a predictive model is trained with only the target learner. The types of analysis may be any supervised data modeling 552, as discussed in the first analysis example above. The difference between the analysis for the first example and the analysis for the second example is that a model is trained with the biometric data that is only generated from the target learner in the second example.

Third Analysis Example

In a third example, general rules are extracted from biometric data and used for many education related tasks. For example, the rules may be used for grouping students that share similar brain functions to the same groups. The biometric data from the group of students may have the appearance of, for example, one certain type or combination of EEG waves responsible for monitoring one brain function. The EEG signal(s) in common may then be used to group students, so that students share similar brain functions will be grouped together. Such grouping will facilitate the education process by orientating the teaching strategy.

As discussed with the previous two examples, any supervised data modeling 552 can be applied here, including non-negative matrix factorization (NMF), Spectral Clustering, K-Means, and/or DB Scan. For general rule extraction, the input data are from all the learners. With an unsupervised data analysis 554 strategy, no labels are required for biometric data. We could still discover the hidden knowledge rules from different biometric data, with the following steps. First biometric data filtering 565 is performed to remove the noisy and not useful signal information. Next, any feature selection or extraction technique 567 is applied to reduce feature dimension. Examples of feature extraction techniques may include SVD or Tf*Idf. Then, the hidden learner subgroups are discovered by applying any clustering method on processed data, for example data analysis module 568 applying the algorithm $\hat{X}=U\Sigma R^{n \times p}$ $X'=U\Sigma \in Rn \times p$. Although any clustering method can be applied here, we use non-negative matrix factorization as an example here, which is defined as $\min_{W,H} \|\hat{X}-WH\|_F$, where given the expected number of learner groups t, we could learn the group indicator matrix $H \in R^{n \times t}$. For example, if $H_{kj}>0$, learner j belongs to the k th group.

Fourth Analysis Example

In a fourth example, a personalized learning pattern may be derived by extracting rules for each individual learner. It is analyzed if any periodical biometric signal pattern appears for any given learner. The analysis may be performed using any unsupervised data analysis 554. For personal rule extraction, the input data are only generated from the target learner. Analysis description is similar as defined in the third analysis example. The difference is that only the biometric data that is generated from the target learner is used in this example system.

The disclosed examples may include systems, devices, computer-readable storage media, and methods facilitating education using biometric data. For purposes of explanation, certain examples are described with reference to the components illustrated in FIGS. 1-3. The functionality of the illustrated components may overlap, however, and may be present in a fewer or greater number of elements and components. Further, all or part of the functionality of illustrated elements may co-exist or be distributed among several geographically dispersed locations. Moreover, the disclosed examples may be implemented in various environments and are not limited to the illustrated examples.

Moreover, as used in the specification and the appended claims, the singular forms "a," "an," and "the" are intended to include the plural forms as well, unless the context indicates otherwise. Additionally, although the terms first, second, etc. may be used herein to describe various elements, these elements should not be limited by this terms. Instead, these terms are used to distinguish one element from another.

Further, the sequence of operations described in connection with FIGS. 1-5 are examples and are not intended to be limiting. Additional or fewer operations or combinations of operations may be used or may vary without departing from the scope of the disclosed examples. Thus, the present disclosure merely sets forth possible examples of implementations, and many variations and modifications may be made to the described examples. All such modifications and variations are intended to be included within the scope of this application and protected by the following claims.

We claim:

1. A system for using biometric data to facilitate learning by an individual, the system comprising:
   a data acquisition engine to obtain at least two data points from biometric sources that monitor the individual while the individual consumes content, wherein the biometric sources include a facial sensor;
   a data aggregation engine to gather a filtered biometric data set by extracting a collection of learning data from the at least two data points;
   a signal processing engine to:
   identify a set of features selected from the filtered biometric data set; and
   a data analysis engine to apply a predictive machine learning model to correlate the set of features to a measure of comprehension of the content by the individual, wherein the predictive machine learning model maps facial changes to measures of comprehension.

2. The system of claim 1, wherein the signal processing engine uses the set of features to generate a feature matrix and performs feature reduction on the feature matrix.

3. The system of claim 2, wherein the data analysis engine applies the predictive machine learning model to the feature matrix and outputs discovered correlations.

4. The system of claim 1, wherein the data aggregation engine removes unnecessary sensor data from the at least two data points.

5. A non-transitory computer-readable storage medium encoded with instructions that, when executed by a processor performs a method, causes the process to:
   receive at least two data points via a biometric sensor that monitors an individual while the individual consumes content, wherein the biometric sensors include a facial sensor;
   extract a collection of learning data from the at least two data points;
   identify a set of features from the collection of learning data and perform feature reduction on the set of features;

apply a predictive machine learning model to analyze the set of features after the feature reduction to correlate the set of features to a measure of comprehension of the content by the individual, wherein the predictive machine learning model maps facial changes to measures of comprehension.

6. The non-transitory computer-readable storage medium of claim 5, wherein the set of features are analyzed using the collection of learning data without applying additional functions.

7. The non-transitory computer-readable storage medium of claim 5, wherein at least one of the at least two data points are obtained from a wearable device.

8. A method to use biometric data to facilitate learning by an individual, the method comprising:
    obtaining at least two types of biometric data via a sensing device that monitors the individual while the individual consumes content;
    extracting a collection of learning data from the at least two types of biometric data;
    selecting a set of features to represent the collection of learning data and removing features from the set of features to form a subset of the set of features; and
    applying, by a data analysis engine, a predictive machine learning model to correlate the subset of the set of features to a measure of comprehension of the content by the individual.

9. The method of claim 8, further comprising applying data fusion technology on the subset of the set of features to categorize the collection of learning data for the individual.

10. The method of claim 8, comprising identifying hidden patterns in the subset of the set of features to obtain a learning characteristic.

11. The method of claim 8, comprising performing predictive modeling on the subset of the set of features to obtain a learning characteristic.

12. The method of claim 8, further comprising removing non-related biometric data to create the set of features.

13. The method of claim 12, further comprising manipulating the set of features by extracting the subset of the set of features identified as corresponding to learning characteristics.

14. The system of claim 1, wherein the predictive machine learning model maps galvanic skin responses to measures of comprehension.

15. The system of claim 1, wherein the predictive machine learning model maps heart rate to measures of comprehension.

16. The system of claim 1, wherein the predictive machine learning model maps neurological responses to measures of comprehension.

* * * * *